United States Patent [19]

Carl

[11] Patent Number: 5,226,462

[45] Date of Patent: Jul. 13, 1993

[54] INTRODUCING MEASURED AMOUNTS OF LIQUID INTO RECEPTACLES

[76] Inventor: Richard A. Carl, 30833 Rue Valois, Rancho Palos Verdes, Calif. 90274

[21] Appl. No.: 736,407

[22] Filed: Jul. 26, 1991

[51] Int. Cl.$^5$ .............................................. G01N 1/14
[52] U.S. Cl. ........................................ 141/1; 141/130; 141/180; 141/181; 141/238; 73/863.32; 73/864.24
[58] Field of Search ................... 141/130, 1, 100, 102, 141/177, 180, 181, 183, 184, 186, 189, 234, 237, 238, 240, 242, 283, 284; 73/863.32, 864.24, 864.17, 864.18; 422/65, 100; 436/47, 180; 222/386; 92/181 R

[56] References Cited

U.S. PATENT DOCUMENTS

| | | | |
|---|---|---|---|
| 2,932,330 | 4/1960 | Donofrio | 141/178 |
| 3,036,604 | 5/1962 | Donofrio | 141/169 |
| 3,202,187 | 8/1965 | Pechmann | 141/93 |
| 3,650,306 | 3/1972 | Lancaster | 141/238 |
| 3,836,329 | 9/1974 | Jordan | 436/49 |
| 4,000,765 | 1/1977 | Lydiksen | 141/181 |
| 4,054,415 | 10/1977 | Seligson et al. | 73/864.24 X |
| 4,135,561 | 1/1979 | Senelonge | 141/234 |
| 4,140,488 | 2/1979 | Mack et al. | 422/100 |
| 4,158,035 | 6/1979 | Haase et al. | 422/100 |
| 4,169,125 | 9/1979 | Rodriguez et al. | 422/65 |
| 4,256,153 | 3/1981 | Lamaziere | 141/84 |
| 4,258,761 | 3/1981 | Bennett, Jr. | 141/242 |
| 4,276,048 | 6/1981 | Leaback | 436/180 |
| 4,313,476 | 2/1982 | Bennett et al. | 141/181 X |
| 4,313,735 | 2/1982 | Yamashita et al. | 436/47 |
| 4,325,909 | 4/1982 | Coulter et al. | 73/864.24 X |
| 4,351,799 | 9/1982 | Gross et al. | 422/100 X |
| 4,478,094 | 10/1984 | Salomaa et al. | 73/863.32 |
| 4,498,510 | 2/1985 | Minshew, Jr. et al. | 141/27 |
| 4,562,871 | 1/1986 | Astle | 141/238 X |
| 4,635,665 | 1/1987 | Namba et al. | 134/167 R |
| 4,685,480 | 8/1987 | Eck | 134/182 |
| 4,803,050 | 2/1989 | Mack | 422/65 |
| 4,913,323 | 4/1990 | Scheindel | 222/386 |
| 4,980,130 | 12/1990 | Metzger et al. | 422/70 |
| 5,021,217 | 6/1991 | Oshikubo | 422/100 |
| 5,035,270 | 7/1991 | Herzog | 141/180 X |

Primary Examiner—Henry J. Recla
Assistant Examiner—Casey Jacyna
Attorney, Agent, or Firm—Charles Berman

[57] ABSTRACT

Introducing a measured amount of a liquid into receptacles in a microtiter plate includes locating receptacles in register with the liquid supply. The liquid supply includes pistons and cylinders operated by a stepper motor for adjustable measured and controllable incremental delivery of amounts of liquid simultaneously to the receptacles. A liquid source is located below the support for the receptacles and the receptacles are transversely moveable on a conveyor away from a filling station so that the liquid can be obtained from the liquid source. Pneumatic means moves both the cylinders and the pistons in the liquid supply upwardly and downwardly relative to the receptacles and the liquid source. The stepper motor moves the pistons upwardly and downwardly relative to the receptacles and liquid source.

27 Claims, 6 Drawing Sheets

INTRODUCING MEASURED AMOUNTS OF LIQUID INTO RECEPTACLES

BACKGROUND

The delivery of precise measurable and adjustable amounts of liquid to receptacles is important. This is particularly so in areas of scientific, chemical and medical analysis.

This invention relates to providing accurate amounts of liquid to receptacles. In particular, the invention is concerned with accurately dispensing multiple amounts of liquid from a liquid supply to multiple receptacles contained in a microtitration plate.

Conventional means for delivering liquid to microtitration plates operate with a system where the liquid supply is controlled by pneumatic, hydraulic or mechanical means. Relatively complex and cumbersome techniques are used for setting these means to adjust the liquid supply. Usually, a system would operate where a platten would move between different mechanical stops. Alternatively, different pneumatic or hydraulic pressure arrangements are used as a determinant of ensuring that the correct amount of liquid is delivered to wells. To adjust the systems, mechanical manipulation of component parts or pressure variations are necessary to adjust or fine-tune the amounts of liquid to be delivered to the wells.

The invention seeks to provide a system for the accurate, adjustable and measurable control of the supply of liquid to receptacles in a manner minimizing the problems of the prior art.

SUMMARY

By the present invention, there is provided a system for introducing a measured amount of liquid into receptacles in a manner which is adjustable and controllable. Incremental measured amounts can be supplied.

According to the invention, the system for controlling the delivery of measured amounts of liquid includes a stepper motor which is computer controlled. The rotation of the motor shaft is controlled to regulate the amount of liquid for supply simultaneously to multiple receptacles lying in a plane formed in two directions. The shaft of the motor can be controllable in its rotation between a portion of a revolution and multiple revolutions. Liquid is drawn into cylinders or expelled from cylinders by the movement of a piston which is actuated by the motor shaft through a platten and is thereby finitely controlled.

By inputting information into the computer representative of the desired volume to be drawn from a liquid source into a liquid supply and inputting information about the amount of liquid volume to be expelled from the liquid supply into the receptacles, accurate amounts of incremently adjustable amounts of liquid into the receptacles is controlled.

In a preferred form of the invention, multiple receptacles are contained in different trays which are transversely serially moveable on conveyor means to and from a filling station. Multiple cylinders and pistons are located in register in a plane above the receptacles and the pistons and cylinders are part of the fluid supply means. The pistons and cylinders are jointly moveable by pneumatic means located below the filling station to operate between the plane formed by the receptacles, a plane formed by a fluid source below the receptacle plane and a plane removed from both these planes.

The fluid supply means is operable additionally by the stepper motor to move the pistons in the cylinders between different positions so that liquid can be drawn into the cylinders and expelled from the cylinders as required.

The invention is directed to the device and method for filling multiple receptacles.

The invention is further described with reference to the accompanying drawings.

DRAWINGS

DESCRIPTION

Figure 1:
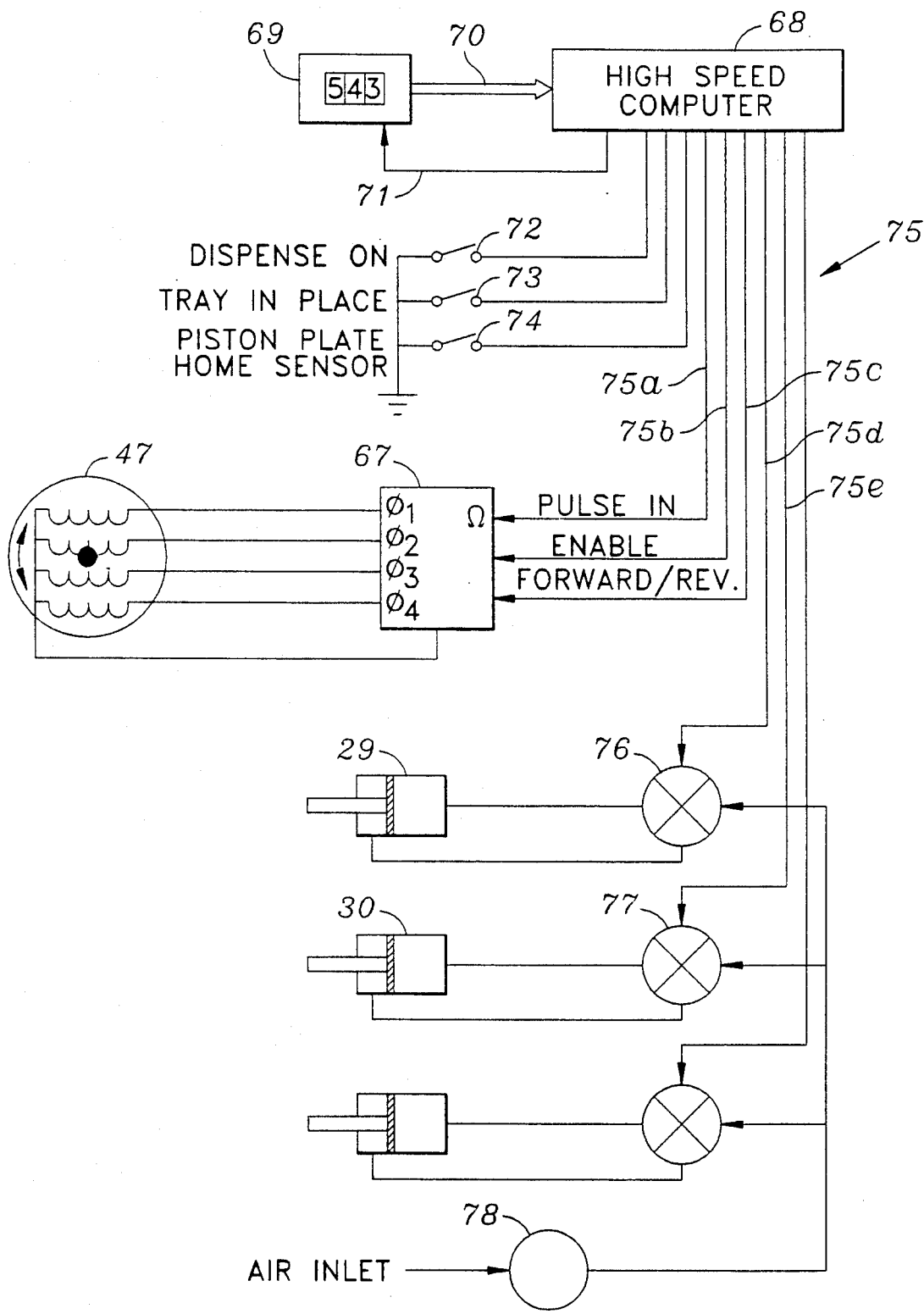
FIG. 1 is a schematic block diagram illustrating the computer interface, computer, stepper motor and air control valves operable by the computer.
Figure 2A:
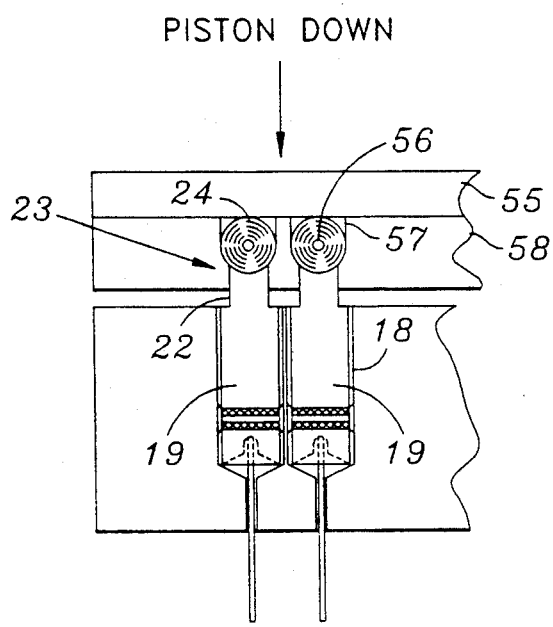
FIG. 2a is a partial sectional elevational view of the pistons in the down position in the cylinder.
Figure 2B:
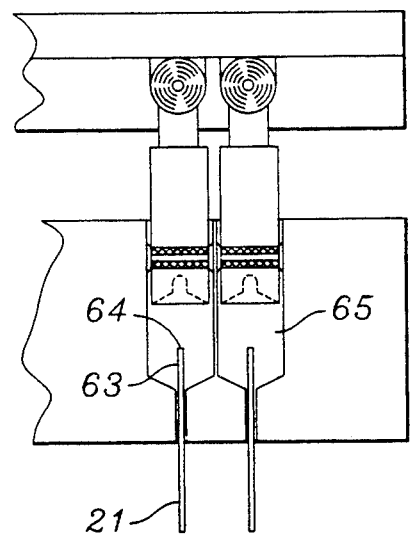
FIG. 2b is a partial sectional elevational view illustrating the pistons and the position.
Figure 2C:
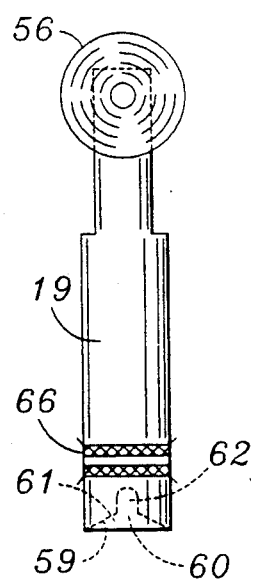
FIG. 2c is a partial elevational view of a piston showing the detail of the bore for engagement with the platten and illustrating the recess and seals.

A system for providing measured amounts of liquid into receptacles 10 comprises support means 11 for the receptacles 10 which are contained in a microtiter tray 12. The support means 11 moves the receptacles 10 transversely towards and from a filling station location 14. The support means 11 is constituted by two spaced endless bands 15a and 15b on which the receptacles 10 in tray 12 rest and move. The tray 12 moves as indicated by arrow 17 so that tray 12 can serially be fed towards and away from the filling station 14 on the conveyor support 11.

Liquid supply means 16 is located above the filling station 14 and the liquid supply means 16 has cylinders 18, with pistons 19 moveable in the cylinders 18. An outlet 20 from each cylinder 18 is in register with the receptacles 10.

As illustrated, there are multiple receptacles 10 located in a rectangular planar configuration and are constituted in the microtiter plate 12. The receptacles 10 are in a plane formed by the direction of travel 17 and also perpendicular to the direction of travel 17.

Needles 21 are provided at the outlets 20 and are similarly located in a rectangular configuration connected at the outlet end of each cylinder 10. The needles 21 are in register with each of the receptacles 10 when the receptacles 10 are located at the filling station 14 below the needles 21.

Each of the pistons 19 is connected with an operating rod 22 which is attached so that it moves the pistons 19 upwardly and downwardly in the cylinder 18. The opposite end 23 of the rod 22 is attached to actuating means 24 such that the pistons 19 are enabled to move relatively in and out of the cylinders 18. Respectively, when the pistons 19 move downwardly in the cylinders 18, liquid is expelled from the cylinders 18. When the pistons 19 move upwardly in the cylinders 18, liquid is drawn into the cylinders 18 from a liquid source 24 located below the support means 11 for the receptacles 10.

The liquid supply means 16 is mounted on four pillars 25, 26, 27 and 28 which are spaced in a substantially rectangular fashion. The pillars 25, 26, 27 and 28 are moveable up and down under action of a pair of pneumatic cylinders 29 and 30 mounted on a base 31 and underneath a support plate 32. As the cylinders 29 and 30 move apart, the rod 33 and 34 can extend as necessary. This moves the liquid supply means 16 and pillars 25, 26, 27 and 28 upwardly and from the liquid source 24 or receptacles 10 as described. When the rods 33 and 34 contract variously, the liquid supply means 16 and pillars 25, 26, 27 and 28 are moved downwardly towards the receptacles 10 and liquid source 24 as described. The pillars 25, 26, 27 and 28 are located in linear bearings 35, 36, 37 and 38 (the latter being behind the top plate 39 in FIG. 3) so that the vertical movement of the fluid supply means 16 can be effected.

The receptacles 10 in the tray 12 move as indicated by arrow 17 on conveyor belts 15 transversely relative to filling station 14. The conveyor is formed essentially by extended O-ring type bands 15a and 15b which are spaced apart. Between the bands 15a and 15b at the level of support table 40 at the filling station 14, there is effectively a space 44. When the receptacles 10 in tray 12 are not in position at the table 40, there is a space 41 below the needles 21. In this fashion, the needles 21 can extend below the level of the table 40 into the liquid source 24 located below the level of table 40. In other cases, when the receptacles 10 in tray 12 are in position as moved by the conveyor system on bands 15a and 15b below the needles 21, the needles 21 extend into the receptacles 10 in tray 12 and not below in the liquid source 24.

Figure 4:
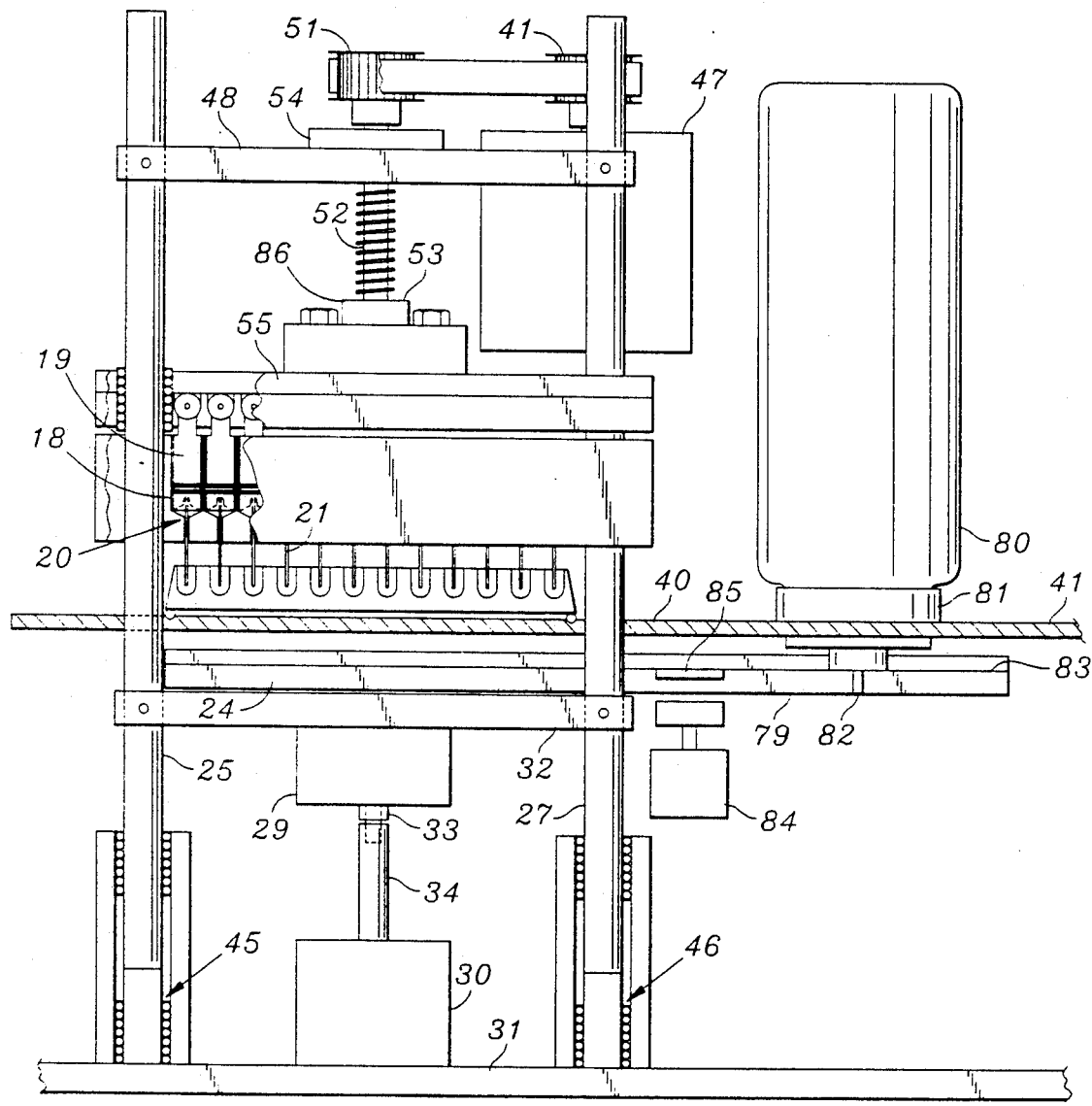
FIG. 4 is a side view illustration of the apparatus with the receptacles in position and needles from the fluid supply system in the receptacle wells, and the pillars being relatively partially extended above the base.
Figure 5:
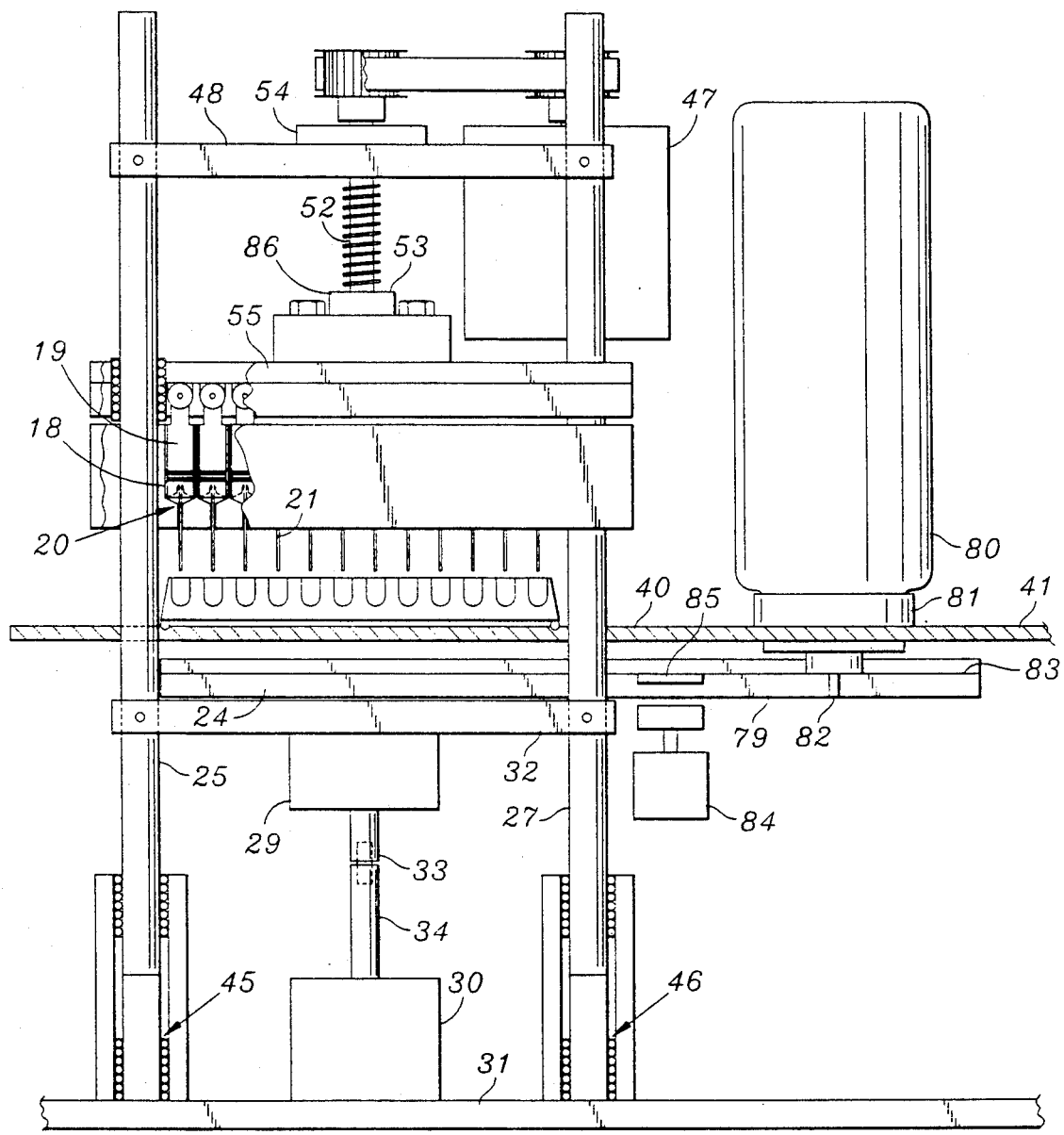
FIG. 5 is a side view of the apparatus with the needles withdrawn above the receptacles and the receptacles in place on the conveyor system support below the needles, and the pillars being relatively further extended above the base.
Figure 6:
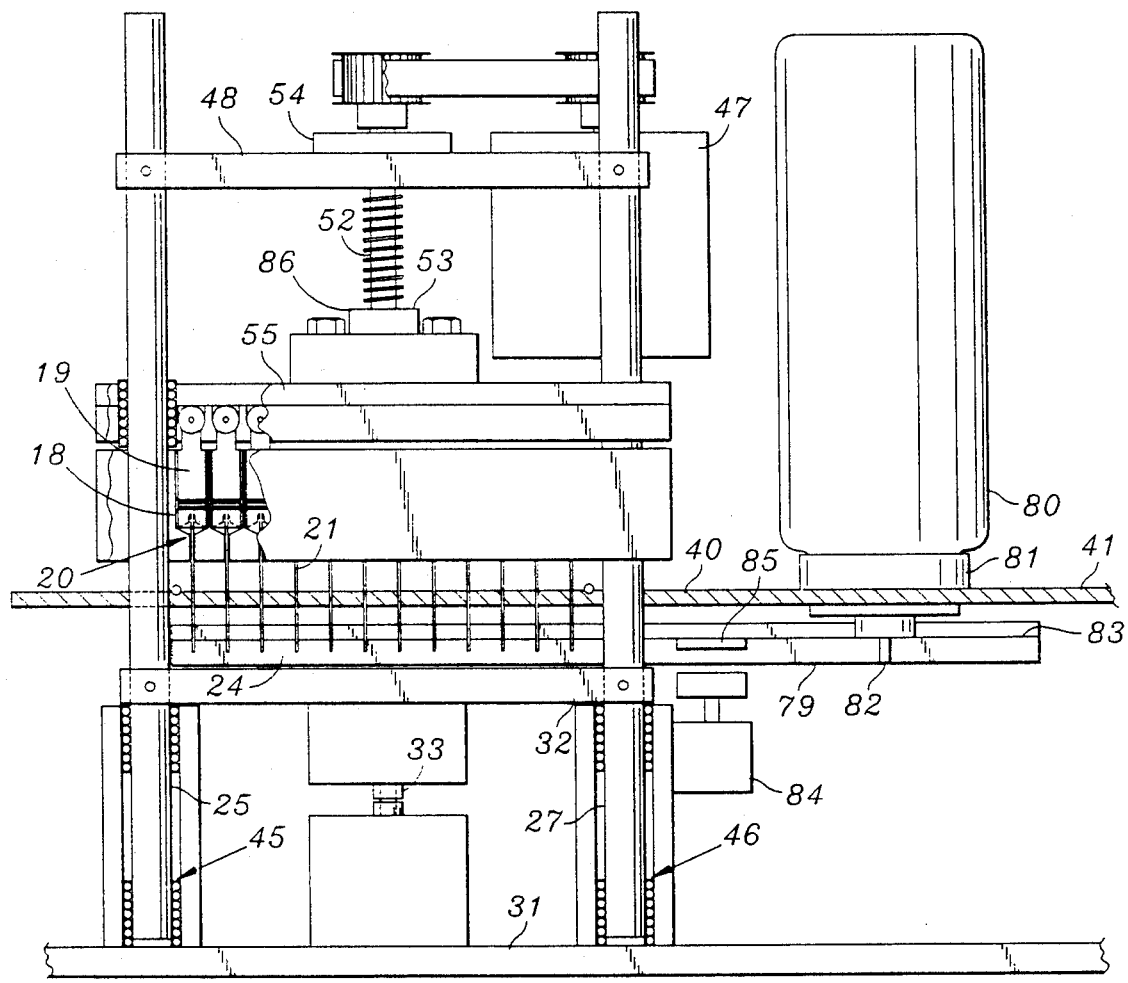
FIG. 6 is a side view of the apparatus illustrating the needles from the fluid supply in the fluid source well wherein the fluid receptacles are not in position below the needles, and the pillars being relatively non-extended and being adjacent the base.

Each of the pillars 25, 26, 27 and 28 is located at their respective bases in further linear bearings. Such bearings are illustrated in FIGS. 4, 5 and 6 by numerals 45 and 46 for the pillars 25 and 27. Similar bearings are located for pillars 26 and 28 and behind the illustrated bearings 45 and 46. As can be seen in comparison between FIGS. 4 and 5 on the one hand and FIG. 6 on the other hand, the pillars in FIGS. 4 and 5 are raised from the base 31 whereas in FIG. 6, the pillars are located substantially adjacent to the base 31.

The stepper motor 47 is mounted above the filling means 16 and below a plate 48 and the shaft of the step is connected to a pulley 49 which drives a pulley belt 50 and in turn, a pulley 51. Pulley 51 can rotate the head of a lead screw 52 so the shaft rotates between a part of a revolution and multiple revolutions and this rotates the pulley 49, which moves the pulley belt 50 and also the pulley 51. This in turn rotates the lead screw 52 as required. The free end 53 of the lead screw is affixed to a lead screw nut 86 in platten 55 after passing through appropriate axial and thrust bearings 54 in plate 48.

Accordingly, as the lead screw 52 moves upwardly and downwardly, so the platten 55 moves upwardly and downwardly. Trapped below the platten 55 is a ball-type device 56 which fits in a mating socket 57. The ball is affixed to the attachment rod 22 which in turn is connected to the pistons 19. The ball device 56 located in 57 permits for fine axial type adjustment of the pistons relative to the support 57 which is formed inside platten 58. The ball allows the piston to travel in an arc about the hole in platten 58. This allows for alignment in all directions between the cylinders and the platten 58.

The free end 59 of the pistons have a recess 60 which is conically formed at 61 and then has an inset slot 62. The needles 21 extend as indicated by 63 to project into the base of the cylinders 18 and the free end 64 of the needles 21 can be accommodated in the recess 61 and 62 as required. When the needles 21 are located in the liquid source 24 and the pistons 19 are urged upwardly and downwardly in the cylinders, air which is trapped in the end 65 of the cylinders is purged from the cylinders 18. Suitable U-cup seals 66 about the pistons 19 effect an appropriate seal with the walls of the cylinders 18.

The stepper motor 47 is controlled through a stepper motor controller driver 67 which is in turn operated by a high speed computer 68. The computer interface 69 inputs information as indicated along by 70 to the computer 68. Feedback information from the computer is cycled back along line 71. Different switches are activated to control the computer. Switch 72 is for indicating that the dispense mode should commence. Switch 73 would indicate that the tray is in location at the filling station. The location of the home position is indicated by closure of switch 74. The pistons 19 are at their lowest position ("home"). When the pistons are "home", this is the reference place for the computer 68 to start all operations. When the computer 68 gets a signal to start the dispense cycle it first makes sure that the home sensor 74 is activated. The stepper motor 47 then starts to draw liquid up into the cylinders 18. When the cycle is completed the pistons 19 reach the home sensor 74, and all fluid is dispensed from the cylinders 18 which ends the entire cycle.

The outputs 75 from the computer respectively are indicated such that 75a indicates the pulse into the controller driver for the motor. Line 75b would be the enable line to the controller. Line 75c is the line to send a forward or reverse signal to the controller for the stepper motor 47. Line 75d activates the air control valve 76 for operating a pneumatic cylinder 29 and line 75e is the line for operating the air control valve 77 for the pneumatic cylinder 30. An air regulator inlet 78 is provided for the air control valve 76 and 77 as indicated.

A liquid source 24 located below the table level 40 is formed in a well 79. The table 40 has an aperture through which a container 80 in inverted position can be placed with the neck 81 in location. In the head of the neck 81 is a spring valve 82. The spring 81 in the neck of the bottle cap closes off the liquid when removing or installing the container 80. The fluid level 83 is maintained by the neck 81 entering into the fluid. Once the fluid closes in around the neck 81 air is not allowed to enter into the container 80. No liquid is allowed to escape into the tray 79 below. The neck 81 protrudes into the liquid thus stopping the supply of air that displaces the liquid in the inside top of the container 80. A motor 84 is mounted relative to the well 79 with an agitator 85. Motor 84 magnetically interacts with the agitator 85 thereby to effect agitation of liquid in the well 79 as part of the liquid source.

Figure 3:
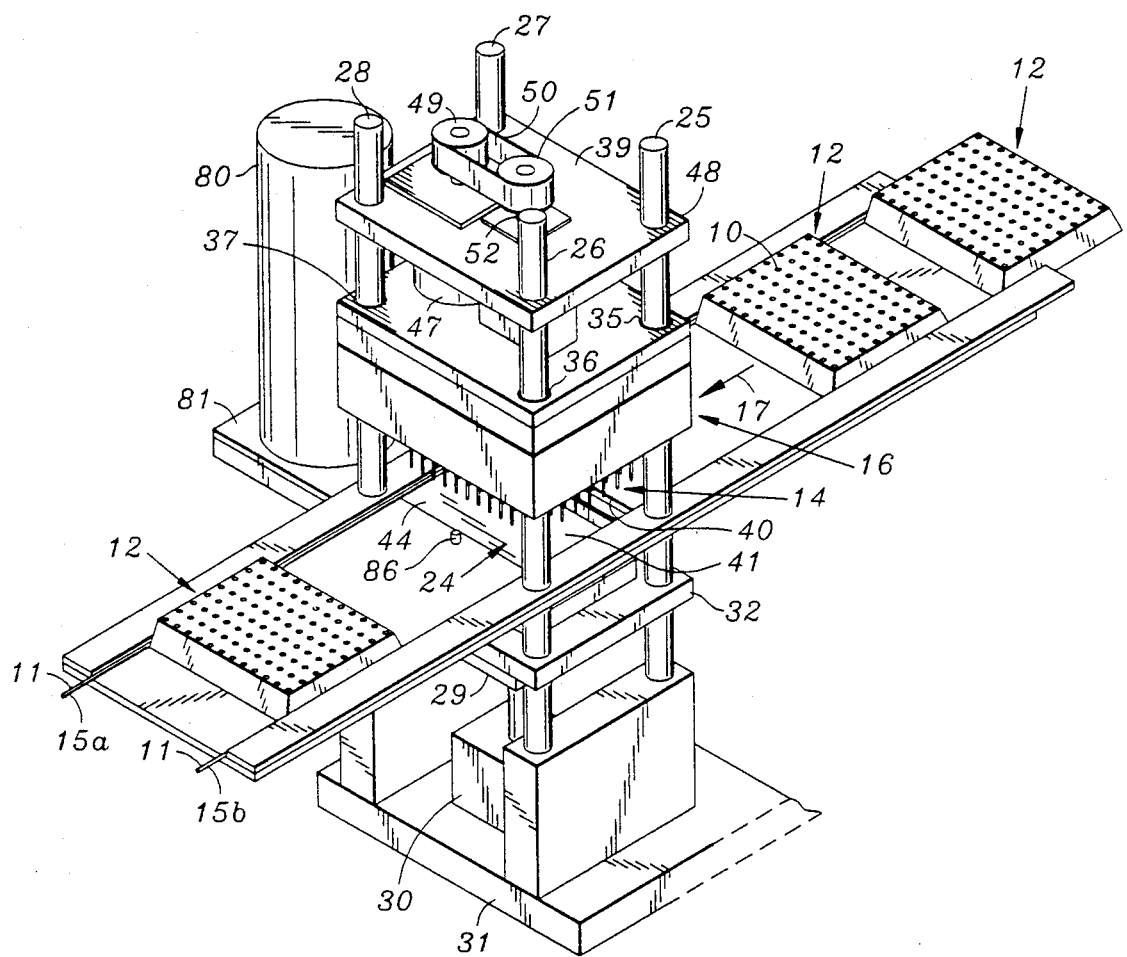
FIG. 3 is a perspective view illustrating the apparatus for providing measured amounts of liquid into the receptacles.

As illustrated in FIG. 3, different microtiter trays can be serially fed to and from the filling station on the conveyor system.

A computer operated pneumatically controlled stop 86 is located downstream of the filling station. When stop 86 projects into the line of travel of the conveyor, the microtiter plates are stopped in the filling station 14. When the stop 86 is withdrawn below the conveyor, the microtiter plates 12 pass from the filling station transversely away from the filling apparatus.

With this apparatus, it is possible to dispense accurately into 96 wells or receptacles of a microtitration plate lo liquid simultaneously in one filling operation. The amount of liquid is precisely regulated by the operator by way of the computer interface 69. The computer 68 controls the motion of the piston plate 55 as part of a platten which has 96 pistons 19 mounted in respectively 96 cylinders 18. The pistons 18 draw fluid from the fluid source located below the filling station 14 and after the microtiter plate 12 is located in the filling station, the action of the piston plate or platten whereby the motor causes the piston to move downwardly into the cylinder dispenses liquid into the receptacles 10 of the plate 12. This is effected through the ends of the needles 21 which are attached to the outlets 20 from the cylinders.

When the needles 21 are located in the wells 79 of the liquid source 24 below the filling station 14, the action of the stepper motor is to draw the pistons upwardly in the cylinders and thereby fluid is drawn into the cylinders.

An operator enters a desired volume into the computer interface 69. The operator then turns on the dispense switch 72 and the computer 68 requests the volume setting from the computer interface device 69. The computer 68 converts the desired volume to a specific number of steps or increments. The computer 68 is programmed with the volume of each step and receives the requested volume from the operator. It then sends out the number of steps to the stepper motor 47 as required for the desired volume. The computer signals are then sent to the stepper motor controller and driver 67.

The controller and driver 67 converts the step pulses from the computer 68 into four phases that causes the stepper motor 47 to make its incremental rotations. The rotational increments of stepper motor 47 are transferred to the lead screw 52. The lead screw 52 is held in place and transfer the torque with the aid of the two bearings 54, namely, the thrust bearing and a lead screw axial bearing. The lead screw 52 is coupled to the piston plate 55 through the lead screw nut 86.

When both the pneumatic cylinders 29 and 30 mounted between base 31 and plate 32 are activated, the entire fluid supply means 16 is raised to its highest position. Conversely, when both the cylinders 29 and 30 are retracted, the fluid supply means 16 is in the lowest position. In the lowest position, the needles 21 pass through the space in the conveyor surface into the liquid source 24. The stepper motor rotates a number of steps as determined by the computer to draw the pistons 19 up and the cylinders 18 so that the required amount of liquid is introduced into the cylinders 18. Thereafter, the pneumatic cylinders 29 and 30 are activated to extend the fluid supply means 16 out of the line of the tray 12 and above the conveyor surface. Thereafter, the tray 12 is located in the filling station 14 and the cylinder 29 retracts, lowering the filling system 16 so that the needles 21 can enter the receptacles 10. Through the stepper motor 47, the requisite number of rotations are effected to dispense liquid into the receptacles 10. Thereafter, the air cylinder 29 is activated to lift the fluid supply means above the receptacles. The tray can then move down the conveyor away from the filling station 14.

By this invention, there is provided a system for simultaneously filling multiple receptacles in a plane defined by the path of travel 17 and perpendicularly to that path of travel. The receptacles 10 can be filled accurately, controllably, adjustably, incrementally and measuredly by means of the computer control of the stepper motor 47. In other systems, it may be possible to use a servo motor with suitable feedback to effect the same control. Moreover, the location of the pneumatic means below the base of the conveyor table minimizes the amount of mass above the table so that the movement of the moveable parts can easily be effected with minimum obstruction.

The mounting of the system on four spaced apart pillars 25, 26, 27 and 28 ensures parallel alignment for three independent operations. These are:

1) The dispense liquid supply means 16 is made up of two planes being plattens 55 and 58 and the block that contains the cylinders 18. These two plattens 55 and 58 and block are retained in alignment at all times as they move up and down the pillars. Should these plattens 55 and 58 move out of parallel, it directly effects the fluid volume in the cylinders 18 and the accuracy of the machine.

2) The needles 21 and the multiple receptacles 12 in the plate 10 are aligned.

3) The needles 21 and the fluid in the liquid source reservoir 24 are aligned.

These three operations, being in parallel alignment, ensure that the multiple receptacles 12 in the plane defined by the direction of travel and the perpendicular direction of the conveyor are simultaneously accurately filled.

A smooth conveying operation is effected in one direction for the receptacle plates so that they can be serially filled as indicated. By having the liquid supply source located beneath the operating table, it is possible to have a system wherein the liquid supply means does not have to travel transversely to collect fluid from a transversely removed position. Instead, just a single repetitive vertical motion is all that is required to obtain fluid from a liquid source and deliver fluid to wells simultaneously and sequentially and serially to further wells in subsequent microtiter plates. An enhanced automatic efficient system for feeding and filling microtiter wells in an adjustable measureable and controllable manner is provided by this invention.

Many other forms of the invention exist, each differing from the other in matters of detail only. The invention is defined by the following claims.

I claim:

1. Apparatus for introducing a measured amount of a liquid into receptacles comprising:
   (a) support means at a filling station for the receptacles;
   (b) means for moving the receptacles transversely towards and from the filling station;
   (c) means for supplying liquid located above the filling station, the means for supplying liquid having cylinders and pistons moveable in respective cylinders, outlets from the cylinders, the outlets being located to be in register with the receptacles when located at the filling station and wherein each piston is recessed in a leading end, the leading end being adjacent the outlet from each cylinder;

(d) a liquid source for liquid;

(e) operating rods attached to the pistons;

(f) means for actuating the operating rod such that the pistons are enabled to move relatively in and out of the cylinders thereby respectively expelling liquid from the cylinders into the receptacles, and drawing liquid into the cylinders from the liquid source when the receptacles are removed from the filling station;

(g) stepper motor means including a rotatable shaft for turning a lead screw thereby to move the actuating means between different positions and effect different positions of the operating rods; and (h) computer means for adjustably controlling the stepper motor means whereby the rotatable shaft is rotatably controllable between a portion of a revolution and multiple revolutions such that the amount of liquid drawn into or expelled from the cylinders is incrementally adjustably measurably controllable.

2. Apparatus as claimed in claim 1 wherein the liquid supply means is relatively moveable towards and away from the filling station, and the liquid source, the liquid source being stationarily located below the liquid supply means.

3. Apparatus as claimed in claim 2 wherein the piston means is additionally moveable relative to the filling station and the liquid source.

4. Apparatus as claimed in claim 1 wherein the operating rods include a portion extending from the cylinders, the portions extending being secured to a platten, the platten being for engaging the lead screw operable by the stepper motor means.

5. Apparatus as claimed in claim 1 including multiple receptacles defining a plane in the direction of receptacle movement towards the filling station and in a direction perpendicular to the direction of movement, and wherein liquid supply means includes corresponding multiple pistons and cylinders such that when the receptacles are located at the filling station, the respective receptacles are located in register with the respective pistons and cylinders such that when the receptacles are located at the filling station, the respective receptacles are located in register with the respective pistons and cylinders, such that the outlets of the respective cylinders are located in register with respective receptacles, and the receptacles are filled simultaneously.

6. Apparatus as claimed in claim 1 including a reservoir for the liquid source, the reservoir being located adjacent the liquid source and including an inverted container, valve means for controlling liquid flow from the container, and agitator means for mixing liquid in a well, the well being for holding the liquid.

7. Apparatus as claimed in claim 1 wherein the outlet from the cylinder including a needle, the needle having an extension into the cylinder and the extension being for location in the piston recess thereby to facilitate purging air trapped in the cylinder during liquid filling operation from the liquid source.

8. Apparatus as claimed in claim 1 wherein the means for moving the receptacles includes conveyor means, the conveyor means being for feeding receptacles in respective trays serially to and from the filling station such that when the receptacles are in place in the filling station, the cylinders are moveable between a position removed from and towards the receptacles and when the receptacles are not located at the filling station, the cylinders are moveable between a position removed from and a position lower than the filling station.

9. Apparatus as claimed in claim 8 including computer operated stop means and feed means for regulating the conveyance of receptacles on the conveyor relative to the filling station.

10. Apparatus as claimed in claim 1 wherein the liquid supply is supported between four spaced pillars and the filling station is also supported between such pillars such that a parallel motion of the liquid supply means between the filling station and the liquid supply means is maintained over the receptacles.

11. Apparatus for introducing a measured amount of a liquid into a receptacle comprising:

(a) support means at a filling station for the receptacles;

(b) means for moving the receptacle transversely towards and from the filling station;

(c) means for supplying liquid located above the filling station, the liquid supply means having at least one cylinder and a piston moveable in the cylinder, and an outlet from the cylinder, the outlet being located to be in register with the receptacle when located at the filling station;

(d) a liquid source for liquid located below the filling station;

(e) an operating rod attached to the piston;

(f) means for actuating the operating rod such that the pistons are enabled to move relatively in and out of the cylinder thereby respectively expelling liquid from the cylinder into the receptacle and drawing liquid into the cylinder from the liquid source;

(g) electrical motor means including a rotatable shaft for turning a lead screw thereby to move the actuating means between different positions and effect different positions of the operating rod, the motor means being selectively a stepper motor;

(h) computer means for adjustably controlling the motor means whereby the rotatable shaft is rotatably controllable between a portion of a revolution and multiple revolutions such that the amount of liquid drawn into or expelled from the cylinders is incrementally adjustably measurably controllable; and (i) pneumatic means located below the liquid source, the pneumatic means being adapted to move the liquid supply means between a position where the cylinders can remove liquid from the liquid source to a position remote from the liquid source.

12. Apparatus as claimed in claim 11 wherein the computer means controls the stepper motor and the pneumatic means to affect the filling of the cylinders from the liquid source.

13. A method for introducing a measured amount of a liquid into receptacles comprising:

(a) supporting receptacles at a filling station;

(b) moving the receptacles transversely towards and from the filling station;

(c) supplying liquid to the filling station, the supply of the liquid utilizing cylinders and pistons moveable in the respective cylinders, and outlets from the cylinders, the outlets being located to be in register with the receptacles when located in the filling station;

(d) supplying liquid to a liquid source located below the filling station;

(e) actuating the pistons to move relatively in and out of the cylinders, thereby respectively drawing liquid into the cylinders from the liquid source and expelling liquid from the cylinders into the receptacles when the receptacles are at the filling station and when the receptacles are removed from the filling station;

(f) rotating a lead screw under action of a stepper motor; and (g) adjustably controlling the motor by a computer whereby the liquid drawn into or expelled from the cylinders is incrementally adjustable measurably controllable, and including moving the liquid supply under action of pneumatic means located below the liquid source, the pneumatic means moving the liquid supply between a position where the cylinders can remove liquid from a liquid source to a position remote from the liquid source and wherein when the receptacles are located at the filling station, the lead screw locates the cylinders relatively closer to or removed from the receptacles.

14. A method as claimed in claim 13 including selectively removing the receptacles from the filling station, moving the liquid supply and liquid source movably relatively towards each other such that liquid from the liquid source can be drawn into the cylinders.

15. A method as claimed in claim 13 including moving the liquid supply relatively towards and away from the filling station.

16. A method as claimed in claim 15 including additionally selectively moving the pistons relatively to the filling station and the liquid source.

17. A method as claimed in claim 13 including having multiple receptacles defining a plane in the transverse direction and perpendicular to the transverse direction and supplying the liquid through multiple pistons and cylinders in a corresponding plane such that when the receptacles are at the filling station, the respective receptacles are located in register with the respective pistons and cylinders, such that the outlets of the cylinders are located in register with respective receptacles and the receptacles are simultaneously filled.

18. A method as claimed in claim 13 including supplying the liquid source from a reservoir, the reservoir being located adjacent the liquid source, and agitating the liquid source.

19. A method as claimed in claim 13 including computer controlling the stepper motor and the pneumatic means to affect the filling of the cylinders from the liquid source.

20. A method as claimed in claim 19 including selectively removing the receptacles from the filling station, moving the liquid supply and liquid source movably relatively towards each other such that liquid from the liquid source can be drawn into the cylinders.

21. A method as claimed in claim 19 including moving the liquid supply relatively towards and away from the filling station.

22. A method as claimed in claim 19 including having multiple receptacles defining a plane in the transverse direction and perpendicular to the transverse direction and supplying the liquid through multiple pistons and cylinders in a corresponding plane such that when the receptacles are at the filling station, the respective receptacles are located in register with the respective pistons and cylinders, such that the outlets of the cylinders are located in register with respective receptacles and the receptacles are simultaneously filled.

23. A method as claimed in claim 19 including supplying the liquid source from a reservoir, the reservoir being located adjacent the liquid source, and agitating the liquid source.

24. A method as claimed in claim 19 including conveyor feeding the receptacles to and from the filling station such that when the receptacles are in place at the filling station, the cylinders are moveable between a position removed from and towards the receptacles and when the receptacles are removed from the filling station, the cylinders are moveable between a position removed from and a position lower than the filling station.

25. A method as claimed in claim 19 including inputting information into the computer related to a selected volume to be discharged into the receptacles and wherein the computer regulates the stepper motor to effect operation of the motor such that the pistons discharge the selected volume to the receptacles.

26. A method as claimed in claim 13 including conveyor feeding the receptacles to and from the filling station such that when the receptacles are in place at the filling station, the cylinders are moveable between a position removed from and towards the receptacles and when the receptacles are removed from the filling station, the cylinders are moveable between a position removed from and a position lower than the filling station.

27. A method as claimed in claim 13 including inputting information into the computer related to a selected volume to be discharged into the receptacles and wherein the computer regulates the stepper motor to effect operation of the motor such that the pistons discharge the selected volume to the receptacles.

* * * * *